United States Patent
Xu et al.

(10) Patent No.: US 12,071,417 B2
(45) Date of Patent: Aug. 27, 2024

(54) METHOD FOR CATALYTICALLY SYNTHESIZING FURANEOL

(71) Applicant: Xiamen Oamic Biotech Co., Ltd., Fujian (CN)

(72) Inventors: Chupei Xu, Fujian (CN); Zhou Zhu, Fujian (CN); Shunchuan Ke, Fujian (CN); Yibin Zhang, Fujian (CN); Gang Liu, Fujian (CN)

(73) Assignee: Xiamen Oamic Biotech Co., Ltd., Fujian (CN)

( * ) Notice: Subject to any disclaimer, the term of this patent is extended or adjusted under 35 U.S.C. 154(b) by 549 days.

(21) Appl. No.: 17/478,998

(22) Filed: Sep. 20, 2021

(65) Prior Publication Data
US 2022/0089558 A1 Mar. 24, 2022

(30) Foreign Application Priority Data
Sep. 18, 2020 (CN) .......................... 202010991773.6

(51) Int. Cl.
*C07D 307/32* (2006.01)
*C07D 307/60* (2006.01)

(52) U.S. Cl.
CPC ................................ *C07D 307/60* (2013.01)

(58) Field of Classification Search
CPC .................................................. C07D 307/32
USPC ......................................................... 549/477
See application file for complete search history.

(56) References Cited

FOREIGN PATENT DOCUMENTS

| EP | 0398417 A1 | 11/1990 |
| JP | S63307869 A | 12/1988 |
| JP | H0248594 A | 2/1990 |

OTHER PUBLICATIONS

Rodin, et al., "Volatile Flavor and Aroma Components of Pineapple, I. Isolation and Tentative Identification of 2,5-Dimethyl-4-Hydroxy-3 (2H)-Furanone", J.Food Sci. 1965, 30(2), 280-285.
Hodge, et al., "Dicarbonyls, Reductones, and Heterocyclics Produced by Reactions of Reducing Sugars with Secondary Amine Salts", American Soc. Brewing Chemists Proc., (1963) 84-92, https://doi.org/10.1080/00960845.1963.12006704.
Wong, et al., "Chemical and Enzymatic Syntheses of 6-Deoxyhexoses. Conversion to 2,5-Dimethyl-4-hydroxy-2,3-dihydrofuran-3-one (Furaneol) and Analogues", J. Org. Chem. 1983, 48, 3493-3497.

*Primary Examiner* — Jeffrey H Murray
(74) *Attorney, Agent, or Firm* — Cooper Legal Group, LLC

(57) ABSTRACT

A method for catalytically synthesizing furaneol, which uses a specific peptide to function as a catalyst, uses rhamnose to function as a raw material, and uses an organic solvent and a phosphate buffer to function as a reaction solvent to be co-heated to prepare furaneol.

10 Claims, 2 Drawing Sheets

Injection results
Peak Summary

| # | Name | Signal description | RT(min) | Peak area | Peak area% | Peak height | Peak height% |
|---|---|---|---|---|---|---|---|
| 1 | | FID2B | 3.562 | 0.880 | 0.010 | 0.325 | 0.12 |
| 2 | | FID2B | 4.362 | 0.765 | 0.009 | 0.223 | 0.08 |
| 3 | | FID2B | 4.484 | 0.448 | 0.005 | 0.112 | 0.04 |
| 4 | | FID2B | 4.834 | 1.047 | 0.012 | 0.134 | 0.05 |
| 5 | | FID2B | 5.317 | 1.236 | 0.014 | 0.265 | 0.10 |
| 6 | | FID2B | 6.455 | 0.860 | 0.010 | 0.130 | 0.05 |
| 7 | | FID2B | 7.413 | 2.021 | 0.023 | 0.211 | 0.08 |
| 8 | | FID2B | 7.745 | 8.206 | 0.094 | 2.570 | 0.97 |
| 9 | | FID2B | 10.854 | 8665.379 | 99.755 | 260.741 | 98.05 |
| 10 | | FID2B | 11.793 | 1.261 | 0.015 | 0.179 | 0.07 |
| 11 | | FID2B | 12.178 | 0.850 | 0.010 | 0.118 | 0.04 |
| 12 | | FID2B | 12.798 | 1.655 | 0.019 | 0.459 | 0.17 |
| 13 | | FID2B | 14.319 | 1.265 | 0.015 | 0.258 | 0.10 |
| 14 | | FID2B | 14.736 | 0.796 | 0.009 | 0.202 | 0.08 |

Fig.2

METHOD FOR CATALYTICALLY SYNTHESIZING FURANEOL

RELATED APPLICATIONS

This application claims priority to Chinese patent application 202010991773.6, filed on Sep. 18, 2020. Chinese patent application 202010991773.6 is incorporated herein by reference.

FIELD OF THE DISCLOSURE

The present disclosure relates to a technical field for synthesizing furaneol, and in particular relates to a method for catalytically synthesizing furaneol.

BACKGROUND OF THE DISCLOSURE

Furaneol has a scientific name of 2,5-dimethyl-4-hydroxy-3(2H) Furanone. Furaneol, is also known as pineapple furanone or strawberry furanone. In 1965, J. O. Rodin et al. [*J. Food Sci.* 1965, 30(2), 280-285.] first isolated furaneol from pineapple juice extract and detected the structure of furaneol. It is widely present in pineapple, strawberry, citrus, and other natural products. Furaneol has a strong, roasted caramel flavor and has obvious flavor-enhancing modification effects in a very small amount, so it is widely used as a flavoring agent for foods, tobaccos, and beverages.

There are abundant carbohydrate resources in nature, and natural furaneol is one of Maillard reaction products of carbohydrates. Therefore, a preparation of furaneol using carbohydrates is always a goal pursued by industries. There are some literature reports on the preparation of furaneol using carbohydrates. In 1963, Hodge et al. [*American Soc. Brewing Chemists Proc.*, (1963) 84.] used L-rhamnose to react with an organic secondary amine (such as dibutylamine, hexahydropyridine), in acetic acid or ethanol as the solvent under heating condition, and the product was separated and recrystallized to obtain furaneol with a yield of 70-80%. Decnop et al. [EP398417] reported that L-rhamnose was reacted with sodium dihydrogen phosphate and sodium hydroxide in the presence of L-lysine or L-hydroxyproline, and the furaneol yields were 38% and 63% respectively, and when L-fucose and L-lysine were used, the yield under the same condition was 61%. Meguro et al. [JP0248594] used glucose as the raw material to obtain 6-deoxy-D-glucopyranose through multiple steps, which was finally refluxed with piperidine/acetic acid to obtain furaneol. Wong et al. [*J. Org. Chem.*, 1983, 48(20):3493] used D-fructose-1,6-bisphosphate to react with α-hydroxy aldehyde under enzyme catalysis to obtain 6-deoxyfructose-1-phosphate, which was further hydrolyzed to obtain 6-deoxyfructose, and it was then reacted with piperidine/acetic acid to obtain furaneol. Ken et al. [JP63307869] reported that 6-deoxyhexose was treated with an organic base to obtain the furaneol in the presence of an ion exchange resin, and the yield was more than 80%.

BRIEF SUMMARY OF THE DISCLOSURE

An objective of the present disclosure is to provide a method for catalytically synthesizing furaneol.

A technical solution of the present disclosure is as follows.

A method for catalytically synthesizing furaneol, comprising:

(1) mixing rhamnose, phosphate buffer with a pH of 5-7, organic solvent, and a peptide, heating to a reflux state after a nitrogen gas replacement, and reacting until a content of the furaneol in an organic phase no longer changes to obtain a material, wherein a reaction temperature is 60-120° C., a reaction time is 3-6 hours, the peptide consists of 2-20 amino acids and the peptide has a molecular weight of no more than 2000 Daltons;

(2) leaving the material obtained in step (1) to stand to be cooled down to obtain an organic phase and an aqueous phase; and (3) recycling an organic solvent in the organic phase obtained in step (2), then distilling under a reduced pressure to obtain the furaneol, and recycling the aqueous phase.

In a preferred embodiment, the rhamnose defines at least one of a levorotation configuration or a dextrorotation configuration.

In a preferred embodiment, the rhamnose comprises at least one crystal water.

In a preferred embodiment, the peptide comprises at least one of alanyl glutamine, diglycine, L-carnosine, glutathione, collagen tripeptide, fish collagen, or soybean oligopeptide.

In a preferred embodiment, the organic solvent comprises at least one of butyl acetate, ethyl acetate, toluene, benzene, or xylene.

In a preferred embodiment, the organic solvent is butyl acetate.

In a preferred embodiment, the phosphate buffer is a $NaH_2PO_4/Na_2HPO_4$ buffer solution.

In a preferred embodiment, the pH of the phosphate buffer is 6-7.

In a preferred embodiment, a mass ratio of the rhamnose to the peptide is 1:0.1-5.

In a preferred embodiment, the reaction temperature is 100° C. and the reaction time is 3 hours in step (1).

The present disclosure has the following advantages.

1. The present disclosure uses a specific peptide to function as a catalyst, uses rhamnose to function as a raw material, and uses an organic solvent and a phosphate buffer to function as a reaction solvent to be co-heated to prepare furaneol. The aqueous phase and the organic phase in the process can be recycled and reused.

2. In the present disclosure, the efficiency of a reaction is high, where the product can be obtained in one step, the operation of the reaction is simple, and the condition is mild.

BRIEF DESCRIPTION OF THE DRAWINGS

FIG. 2 shows further information regarding the gas chromatography (GC) spectrum of FIG. 1.

DETAILED DESCRIPTION OF THE EMBODIMENTS

Figure 1:
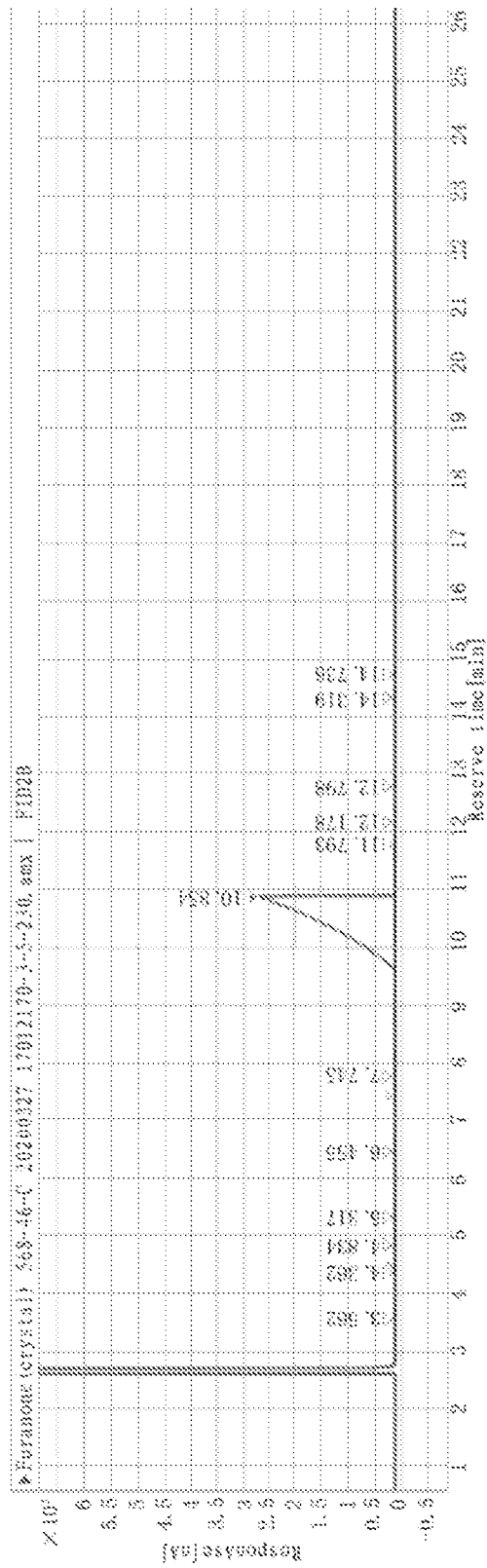
FIG. 1 illustrates a gas chromatography (GC) spectrum of a furaneol prepared in Embodiment 1 of the present disclosure and after recrystallization (ethyl ester is used as a dilution solvent).

The present disclosure will be further described in combination with the accompanying embodiments and drawings.

Embodiment 1

(1) 100 g of rhamnose monohydrate, 600 g of $NaH_2PO_4/Na_2HPO_4$ buffer solution with a pH of 6-7, 500 g of butyl acetate, and 95.8 g of alanyl glutamine are mixed, heated to a reflux state after a nitrogen gas replacement, and reacted until a content of furaneol in an organic phase does not change. A reaction temperature is 100° C. and a reaction time is 3 hours.

(2) The material obtained in step (1) is left to stand and cooled to room temperature (e.g., 20-30° C.) to obtain an organic phase and an aqueous phase.

(3) The organic phase obtained in step (2) is concentrated using rotary evaporation to recycle butyl acetate and to be further distilled in reduced pressure to obtain 25 g of furaneol (a yield is 35%, a GC content is 90% (weight/weight), which reaches 99.7% (weight/weight) after a recrystallization using 95% ethanol. Referring to FIG. 1, a melting point is 77-80° C.). The aqueous phase is recycled for use.

Embodiment 2

The alanyl glutamine obtained in step (1) is replaced with other peptides, and the reaction time and a mass ratio of a peptide to the rhamnose are changed. The rest is the same as Embodiment 1. Experimental results are illustrated in Table 1.

TABLE 1

Reaction conditions for catalytically preparing the furaneol using the rhamnose under different peptides

| Embodiments | Catalyst | Catalyst/ Rhamnose (mass/mass) | Reaction time (hour) | Yield (%) |
|---|---|---|---|---|
| 1 | Alanyl glutamine | 0.958 | 3 | 35 |
| 2 | Alanyl glutamine | 0.958 | 6 | 34 |
| 3 | Diglycine | 0.58 | 3 | 33 |
| 4 | Diglycine | 0.58 | 6 | 32 |
| 5 | L-carnosine | 1 | 3 | 34 |
| 6 | L-carnosine | 1 | 6 | 28 |
| 7 | Glutathione | 1.35 | 3 | 36 |
| 8 | Glutathione | 1.35 | 6 | 35 |
| 9 | Collagen tripeptide | 1 | 3 | 15 |
| 10 | Collagen tripeptide[a] | 1 | 6 | 20 |
| 11 | Fish collagen[b] | 1 | 3 | 16 |
| 12 | Soybean oligopeptides[c] | 1 | 3 | 18 |

Remark:
[a] The collagen tripeptide is a tripeptide consisting of glycine, proline (or hydroxyproline), and another amino acid. A structure of the collagen tripeptide is simply represented as Gly-x-y, and an average molecular weight of the collagen tripeptide is 280 Daltons.
[b] The fish collagen is extracted from fresh skins or scales of deep-sea cods using bioenzymic directing degrading technology and is mainly I-typed collagen. The product is rich in 19 amino acids and has a molecular weight of 800-1200 Daltons (The fish collagen is obtained from Jiangsu Xinrui Biological Technology Co., Ltd).
[c] The soybean oligopeptides is prepared by an enzymatic hydrolysis of soybean protein and is a short-chain polypeptide mainly comprising 2-10 amino acids and having a molecular weight of below 1000 Daltons (The soybean oligopeptides are obtained from Jiangsu Xinrui Biological Technology Co., Ltd.).

The aforementioned embodiments are merely some embodiments of the present disclosure, and the scope of the disclosure is not limited thereto. Thus, it is intended that the present disclosure cover any modifications and variations of the presently presented embodiments provided they are made without departing from the appended claims and the specification of the present disclosure.

What is claimed is:

1. A method for catalytically synthesizing furaneol, comprising:
    (1) mixing rhamnose, phosphate buffer with a pH of 5-7, organic solvent, and a peptide, heating to a reflux state after a nitrogen gas replacement, and reacting until a content of the furaneol in an organic phase no longer changes to obtain a material, wherein a reaction temperature is 60-120° C., a reaction time is 3-6 hours, the peptide consists of 2-20 amino acids and the peptide has a molecular weight of no more than 2000 Daltons;
    (2) leaving the material obtained in step (1) to stand to be cooled down to obtain an organic phase and an aqueous phase; and
    (3) recycling an organic solvent in the organic phase obtained in step (2), then distilling under a reduced pressure to obtain the furaneol, and recycling the aqueous phase.

2. The method according to claim 1, wherein the rhamnose defines at least one of a levorotation configuration or a dextrorotation configuration.

3. The method according to claim 1, wherein the rhamnose comprises at least one crystal water.

4. The method according to claim 1, wherein the peptide comprises at least one of alanyl glutamine, diglycine, L-carnosine, glutathione, collagen tripeptide, fish collagen, or soybean oligopeptide.

5. The method according to claim 1, wherein the organic solvent comprises at least one of butyl acetate, ethyl acetate, toluene, benzene, or xylene.

6. The method according to claim 1, wherein the organic solvent is butyl acetate.

7. The method according to claim 1, wherein the phosphate buffer is a $NaH_2PO_4/Na_2HPO_4$ buffer solution.

8. The method according to claim 1, wherein the pH of the phosphate buffer is 6-7.

9. The method according to claim 1, wherein a mass ratio of the rhamnose to the peptide is 1:0.1-5.

10. The method according to claim 1, wherein the reaction temperature is 100° C. and the reaction time is 3 hours in step (1).

* * * * *